(12) United States Patent
Hahn et al.

(10) Patent No.: US 8,143,296 B2
(45) Date of Patent: Mar. 27, 2012

(54) THIAZOLE-BASED COMPOUND AND INHIBITOR OF T-TYPE CALCIUM CHANNEL CONTAINING THE SAME

(75) Inventors: Hoh-Gyu Hahn, Seoul (KR); Dong-Yun Shin, Seoul (KR); Kee-Dal Nam, Seoul (KR)

(73) Assignee: Korea Institute of Science and Technology, Hawolgok-Dong, Seongbuk-Gu, Seoul (KR)

( * ) Notice: Subject to any disclaimer, the term of this patent is extended or adjusted under 35 U.S.C. 154(b) by 462 days.

(21) Appl. No.: 12/376,599

(22) PCT Filed: Dec. 8, 2006

(86) PCT No.: PCT/KR2006/005345
§ 371 (c)(1), (2), (4) Date: Feb. 6, 2009

(87) PCT Pub. No.: WO2008/018655
PCT Pub. Date: Feb. 14, 2008

(65) Prior Publication Data
US 2010/0179201 A1 Jul. 15, 2010

(30) Foreign Application Priority Data
Aug. 7, 2006 (KR) .................. 10-2006-0074201

(51) Int. Cl.
| A01N 43/78 | (2006.01) |
| A01N 37/52 | (2006.01) |
| A61K 31/425 | (2006.01) |
| A61K 31/155 | (2006.01) |
| C07D 277/00 | (2006.01) |
| C07C 277/00 | (2006.01) |
| C07C 279/00 | (2006.01) |

(52) U.S. Cl. ......... 514/370; 514/634; 548/182; 564/230
(58) Field of Classification Search .................. 514/370, 514/635; 548/182; 564/230
See application file for complete search history.

(56) References Cited

U.S. PATENT DOCUMENTS
5,405,848 A 4/1995 Sanfilippo et al.
6,274,738 B1 * 8/2001 Kozlowski et al. ........... 548/148

FOREIGN PATENT DOCUMENTS
| EP | 0 003 640 A2 | 8/1979 |
| EP | 0 089 730 A2 | 9/1983 |
| JP | 59225172 A * | 12/1984 |
| JP | 09-059258 A | 3/1997 |

OTHER PUBLICATIONS

Morissette et al. "High-throughput crystallization: polymorphs, salts, co-crystals and solvates of pharmaceutical solids" Advanced Drug Delivery Reviews, 2004, vol. 56, pp. 275-300.*
•LaMattina, J. L. et al., Antiulcer agents. '4-Substituted 2-guanidinothiazoles: Reversible, Competitive, and Selective Inhibitors of Gastric H+,K+-ATPase', Journal of Medicinal Chemistry, 1990, vol. 33, No. 2, pp. 543-552, ISSN 0022-2623.
•Srivastava, P. K.; Mehra, S. C., Synthesis of N-Aryl-N'-2-(thiazolyl-, naphthothiazolyl-, -benzothiazolyl)guanidine Hydrochlorides, Journal of Chemical and Engineering Data, 1978, vol. 23, No. 2, pp. 177-178, ISSN 0021-9568.

* cited by examiner

Primary Examiner — Sreeni Padmanabhan
Assistant Examiner — Kendra D Carter
(74) Attorney, Agent, or Firm — Lexyoume IP Group, PLLC

(57) ABSTRACT

The present invention relates to novel thiazole-based compounds and T-type calcium channel inhibitors containing the compound. The T-type calcium channel inhibitor of the present invention is useful as a treating agent for disease associated with overexpression of T-type calcium channel.

5 Claims, No Drawings

THIAZOLE-BASED COMPOUND AND INHIBITOR OF T-TYPE CALCIUM CHANNEL CONTAINING THE SAME

CROSS REFERENCE TO RELATED APPLICATION

This application claims priority to and the benefit of Korean Patent Application No. 2006-0074201 filed on Aug. 7, 2006, which is hereby incorporated by reference for all purposes as if fully set forth herein.

BACKGROUND OF THE INVENTION (a) Field of the Invention

The present invention relates to thiazole-based compounds represented by following Chemical Formula 1, and T-type calcium channel inhibitors containing the compound. The T-type calcium channel inhibitors according to the present invention are useful as a treating agent of diseases associated with over-expression of T-type calcium channel.

[Chemical Formula 1]

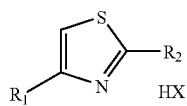

(b) Description of the Related Art

T-type calcium channel is a kind of voltage-dependent calcium channels, which plays an important role in regulating intracellular calcium level at depolarization. As coding genes for the voltage-dependent calcium channels, ten (10) genes have been found, which may be classified into two (2) families, a high voltage activated (HVA) family and a low voltage activated (LVA) family, according to the intensity of the activating voltage. The voltage-dependent calcium channels may be classified into three (3) families, L-type channels (Cav1), P/Q-type and N-type (nervous unit) channels (Cav2), and T-type channels, wherein the L-type channels, and P/Q-type and N-type channels belong to the high voltage activated family, and the T-type channels belong to the low voltage activated family (Ertel et al., 2000).

T-type calcium channel is characterized by low-voltage activated calcium current, rapid activation and slow inactivation. Up to date, as coding genes for the T-type calcium channel, three (3) genes have been identified, and named as α1G (Cav3.1), α1H (Cav3.2), and α1I (Cav3.3), respectively (Cribbs et al., 1998; Perez-Reyes et al., 1998; Klugbauer et al., 1999; Lee et al., 1999; Monteil et al., 2000). The T-type calcium channels may be expressed in whole body, such as a nervous tissue, heart, kidney, smooth muscle, and endocrine organ. The T-type calcium channels have been found to have the functions to regulate bursting firing of nervous cells (Huguenard, J. R. et al., Annu. Rev. Physiol. 1996, 58, 329-348), heart pacemaker activity (Zhou, Z et al., J. Mol. Cell. Cardiol. 1994, 26, 1211-1219), secretion of hormone aldosterone (Rossier, M. F. et al., Endocrinology 1996, 137, 4817-4826) and fertilization (Arnoult, C. et al., Proc. Natl. Acad. Sci. 1996, 93, 13004-13009). Recently, it has been revealed that the T-type calcium channels are also associated with pain signaling (Ikeda, H. et al., Science, 2003, 299, 1237-1240).

The relationship between the expression of the T-type calcium channel and various diseases has been found. The expression of the T-type calcium channel in brain is found to be associated with nociception and repetitive low threshold firing. Especially, a recent study reported a direct relationship between the expression of the T-type calcium channel and pain using a knock-out mouse wherein T-type calcium channel is deleted (Bourinet E. et al., EMBO, 2005, 24, 315-324; Shin, H. S. et al., Science, 2003, 302, 117-119). In addition, the T-type calcium channel is associated with epilepsy. Absent seizure, which is a type of epilepsy, is caused by over-activation of T-type calcium channel in brain (Tsakiridou E et al., J. Neurosci. 1995, 15, 3110-3117). Ethosuccimide is an inhibitor against T-type calcium channel, and has been used in treatment of absence seizure. T-type calcium channel is commonly expressed in heart and smooth muscle, and thus, the inhibitors thereof can be also useful in treatment of hypertension, angina pectoris, and arrhythmia. Recently, it has been found that the T-type calcium channel is associated with the invasion and metathesis of cancer cells, and thus, the inhibitors thereof may be useful as anticancer drugs (Petty, H. R. et al., US 20060003020A1; McCalmont, W. F. et al, Bioorg. Med. Chem. Lett. 2004, 14, 3691-3695).

The exemplary inhibitor against the T-type calcium channel is miberefradil (Posicor®) developed by Roche. Mibefradil, which is a non-dihydropyridine calcium channel inhibitor, obtained FDA approval as a treating drug against hypertension and angina pectoris in 1997. However, Mibefradil has been voluntarily removed since 1999 because of its side effect caused by drug-drug interaction by CYP 3A4 enzyme inhibition.

Therefore, efficient T-type calcium channel inhibitors have not been developed yet. In view of the effects of T-type calcium channel on nerve, pain, epilepsy, hypertension, angina pectoris, heart muscle diseases, blood vessels, cancer metathesis, it has been required to develop efficient T-type calcium channel inhibitors capable of preventing and treating various T-type calcium channel associated diseases by inhibiting the over-expression and over-activation of T-type calcium channel.

SUMMARY OF THE INVENTION

To satisfy the above request, the object of the present invention is to provide novel thiazole-based compounds having T-type calcium channel inhibiting activity, and T-type calcium channel inhibitors containing the compound.

DETAILED DESCRIPTION OF THE PREFERRED EMBODIMENTS

A more complete appreciation of the invention, and many of the attendant advantages thereof, will be readily apparent as the same becomes better understood by reference to the following detailed description.

The present invention relates to thiazole-based compounds represented by following Chemical Formula 1, and T-type calcium channel inhibitors containing the thiazole-based compound. The T-type calcium channel inhibitors according to the present invention may be useful in treatment of various diseases associated with the over-expression of T-type calcium channel.

At first, the present invention provides thiazole-based compounds represented by following Chemical Formula 1:

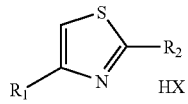

wherein
R1 is

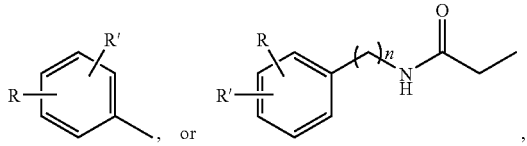

R and R' are the same or different for each other, and independently selected from the group consisting of hydrogen atom, halogen atom, C1-C5 alkyl, alkyloxy, phenyloxy, nitro, cyano, alkoxycarbonyl, and C3-C6 cycloalkyl,
n is 0, 1, or 2,
R2 is

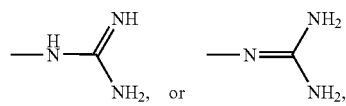

X is halogen atom.

In a preferable embodiment of the present invention, the compounds may be represented by following Chemical Formula 2 or 3:

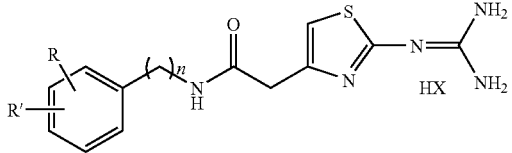

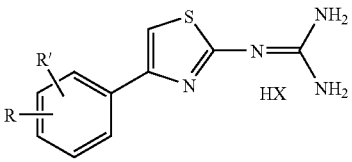

wherein R, R', X and n are the same as defined above.

In an embodiment of the present invention, the thiazole-based compound may be selected from the group consisting of the following compounds:

[2-(2-(diaminomethyleneamino)thiazole-4-yl)-N-(2-fluoro-5-nitrophenyl)acetamide hydrochloride];
N-(2-chloro-4-fluorophenyl)-2-(2-(diaminomethyleneamino)thiazole-4-yl)acetamide hydrochloride;
N-(3-chloro-4-methylphenyl)-2-(2-(diaminomethyleneamino)thiazole-4-yl)acetamide hydrochloride;
2-(2-(diaminomethyleneamino)thiazole-4-yl)-N-(4-fluorophenyl)acetamide hydrochloride;
N-(5-chloro-2-fluorophenyl)-2-(2-(diaminomethyleneamino)thiazole-4-yl)acetamide hydrochloride;
N-(4-chloro-2-fluorophenyl)-2-(2-(diaminomethyleneamino)thiazole-4-yl)acetamide hydrochloride;
N-(2-chloro-4-methylphenyl)-2-(2-(diaminomethyleneamino)thiazole-4-yl)acetamide hydrochloride;
2-(2-(diaminomethyleneamino)thiazole-4-yl)-N-p-tolylacetamide hydrochloride;
N-(4-cyanophenyl)-2-(2-(diaminomethyleneamino)thiazole-4-yl)acetamide hydrochloride;
2-(2-(diaminomethyleneamino)thiazole-4-yl)-N-phenylacetamide hydrochloride;
N-(4-bromophenyl)-2-(2-(diaminomethyleneamino)thiazole-4-yl)acetamide hydrochloride;
2-(2-(diaminomethyleneamino)thiazole-4-yl)-N-(3-fluoro-4-methoxyphenyl)acetamide hydrochloride;
N-(4-chlorophenyl)-2-(2-(diaminomethyleneamino)thiazole-4-yl)acetamide hydrochloride;
2-(2-(diaminomethyleneamino)thiazole-4-yl)-N-(3,5-dichlorophenyl)acetamide hydrochloride;
2-(2-(diaminomethyleneamino)thiazole-4-yl)-N-(4-ethylphenyl)acetamide hydrochloride;
2-(2-(diaminomethyleneamino)thiazole-4-yl)-N-(4-methylbenzyl)acetamide hydrochloride;
2-(2-(diaminomethyleneamino)thiazole-4-yl)-N-(4-methylphenethyl)acetamide hydrochloride;
2-(2-(diaminomethyleneamino)thiazole-4-yl)-N-(3,4-difluorobenzyl)acetamide hydrochloride;
2-(2-(diaminomethyleneamino)thiazole-4-yl)-N-(4-fluorophenethyl)acetamide hydrochloride;
N-(2-bromo-4-methylphenyl)-2-(2-(diaminomethyleneamino)thiazole-4-yl)acetamide hydrochloride;
N-(4-ethoxyphenyl)-2-(2-(diaminomethyleneamino)thiazole-4-yl)acetamide hydrochloride;
2-(2-(diaminomethyleneamino)thiazole-4-yl)-N-(4-isopropylphenyl)acetamide hydrochloride;
2-(2-(diaminomethyleneamino)thiazole-4-yl)-N-(4-nitrophenyl)acetamide hydrochloride;
N-(4-decylphenyl)-2-(2-(diaminomethyleneamino)thiazole-4-yl)acetamide hydrochloride;
ethyl 3-(2-(2-(diaminomethyleneamino)thiazole-4-yl)acetamido)benzoate hydrochloride;
2-(2-(diaminomethyleneamino)thiazole-4-yl)-N-(4-hexylphenyl)acetamide hydrochloride;
N-(4-butoxyphenyl)-2-(2-(diaminomethyleneamino)thiazole-4-yl)acetamide hydrochloride;
ethyl 4-(2-(2-(diaminomethyleneamino)thiazole-4-yl)acetamido)benzoate hydrochloride;
2-(2-(diaminomethyleneamino)thiazole-4-yl)-N-(4-hexylphenyl)acetamide hydrochloride;
N-(4-(cyanomethyl)phenyl)-2-(2-(diaminomethyleneamino)thiazole-4-yl)acetamide hydrochloride;
N-(4-butylphenyl)-2-(2-(diaminomethyleneamino)thiazole-4-yl)acetamide hydrochloride;
2-(2-(diaminomethyleneamino)thiazole-4-yl)-N-(4-phenoxyphenyl)acetamide hydrochloride;
2-(2-(diaminomethyleneamino)thiazole-4-yl)-N-(2,6-dichloro-4-(trifluoromethyl)phenyl)acetamide hydrochloride;
2-(2-(diaminomethyleneamino)thiazole-4-yl)-N-(2,3,4-trifluorophenyl)acetamide hydrochloride;
2-(2-(diaminomethyleneamino)thiazole-4-yl)-N-(4-methoxy-2-methylphenyl)acetamide hydrochloride;
N-(3,5-bis(trifluoromethyl)phenyl)-2-(2-(diaminomethyleneamino)thiazole-4-yl)acetamide hydrochloride;
2-(2-(diaminomethyleneamino)thiazole-4-yl)-N-(2,3,5,6-tetrachlorophenyl)acetamide hydrochloride;
N-(3-chloro-4-methylphenyl)-2-(2-(diaminomethyleneamino)thiazole-4-yl)acetamide hydrochloride;

2-(2-(diaminomethyleneamino)thiazole-4-yl)-N-(2,6-dichloro-4-(trifluoromethoxy)phenyl)acetamide hydrochloride;
2-(2-(diaminomethyleneamino)thiazole-4-yl)-N-(3-fluoro-4-methoxyphenyl)acetamide hydrochloride;
2-(4-(2-oxo-2,3-dihydrobenzo[d]oxazole-6-yl)thiazole-2-yl)guanidine hydrochloride;
2-(5-(4-fluorobenzyl)-4-methylthiazole-2-yl)guanidine hydrochloride;
2-(4-(4-chlorophenyl)thiazole-2-yl)guanidine hydrochloride;
2-(4-(4-fluorophenyl)thiazole-2-yl)guanidine hydrochloride;
2-(4-(2,4-difluorophenyl)thiazole-2-yl)guanidine hydrochloride;
2-(4-(3-oxo-3,4-dihydro-2H-benzo[b][1,4]oxazine-7-yl)thiazole-2-yl)guanidine hydrochloride;
2-(4-(biphenyl-4-yl)thiazole-2-yl)guanidine hydrochloride;
2-(4-(naphthalene-2-yl)thiazole-2-yl)guanidine hydrochloride;
2-(4-p-tolylthiazole-2-yl)guanidine hydrobromide;
2-(4-(4-methoxyphenyl)thiazole-2-yl)guanidine hydrobromide;
2-(4-(2-chlorophenyl)thiazole-2-yl)guanidine hydrobromide;
2-(4-(2-methoxyphenyl)thiazole-2-yl)guanidine hydrobromide;
2-(4-(4-nitrophenyl)thiazole-2-yl)guanidine hydrobromide;
2-(4-(2,4-dimethoxyphenyl)thiazole-2-yl)guanidine hydrobromide;
2-(4-(2-fluoro-4-methoxyphenyl)thiazole-2-yl)guanidine hydrobromide;
2-(4-(2,4-dichlorophenyl)thiazole-2-yl)guanidine hydrobromide;
2-(4-phenylthiazole-2-yl)guanidine hydrobromide;
2-(4-(4-bromophenyl)thiazole-2-yl)guanidine hydrobromide;
2-(4-m-tolylthiazole-2-yl)guanidine hydrobromide;
2-(4-(3-fluorophenyl)thiazole-2-yl)guanidine hydrobromide;
2-(4-(2-fluorophenyl)thiazole-2-yl)guanidine hydrobromide;
2-(4-(3-(trifluoromethyl)phenyl)thiazole-2-yl)guanidine hydrobromide;
2-(4-(3-bromophenyl)thiazole-2-yl)guanidine hydrobromide;
2-(4-(4-ethylphenyl)thiazole-2-yl)guanidine hydrobromide;
2-(4-(3-chlorophenyl)thiazole-2-yl)guanidine hydrobromide;
2-(4-(4-nitrophenyl)thiazole-2-yl)guanidine hydrobromide;
2-(4-(3,4-dichlorophenyl)thiazole-2-yl)guanidine hydrobromide;
2-(4-(2,5-difluorophenyl)thiazole-2-yl)guanidine hydrobromide;
2-(4-(3,5-bis(trifluoromethyl)phenyl)thiazole-2-yl)guanidine hydrobromide.

The thiazole-based compounds of the present invention have excellent T-type calcium channel inhibiting activities, as shown in the experimental examples below. As described above, since the over-expression or over-activation of T-type calcium channel may cause pain, epilepsy, hypertension, angina pectoris, heart muscle disease, vascular disorder, cancer metathesis, and the like, the thiazole-based compounds of the present invention can be used in preventing or treating such diseases.

Therefore, the present invention provides a composition for inhibiting T-type calcium channel containing the thiazole-based compound represented by Chemical Formula 1, 2 or 3, or pharmaceutically acceptable salt thereof. Further, the present invention provides a composition for preventing or treating a disease selected from the group consisting of nervous disease, pain, epilepsy, hypertension, angina pectoris, heart muscle disease, vascular disorder, and cancer.

The amount of the thiazole-based compound contained in the composition according to the present invention may be approximately 0.1 to 99 wt %, but more preferably, properly controlled according to its usage. Further, the administration dosage may be determined considering age, sexuality and condition of patient, absorption and inactivation rates in the body of the active ingredient, and co-administered drugs. For example, the dosage of the composition may be 2 mg/kg (body weight) to 500 mg/kg based on the active ingredient.

The composition according to the present invention may contain the thiazole-based compound with or without other pharmaceutically acceptable drugs, carriers, or excipients. The carriers and excipients used in the present invention may be properly selected depending on the intended formulation type of the composition, for example, including conventional diluents, fillers, expanders, wetting agents, disintegrants, and/or surfactants. Representative diluents or excipients may include water, dextrin, calcium carbonate, lactose, propylene glycol, liquid paraffin, talc, isomerized sugar, sodium metabisulfite, methylparaben, propylparaben, magnesium stearate, milk sugar, normal saline, flavorings and colorants.

The composition according to the present invention may be used as drugs, food additives, or food. When the composition is used as drugs, the composition may be administered in oral or parenteral pathway. The formulation type of the composition may vary depending on its usage. For example, the composition may be formulated in the form of plasters, granules, lotions, powders, syrups, liquids, solutions, aerosols, ointments, fluid extracts, emulsions, suspensions, infusions, tablets, injections, capsules, pills, and the like.

The present invention is further explained in more detail with reference to the following examples. These examples, however, should not be interpreted as limiting the scope of the present invention in any manner.

EXAMPLE

Example 1

Synthesis of the Compound of Chemical Formula 2

The compound of following Chemical Formula 2 was synthesized:

[Chemical Formula 2]

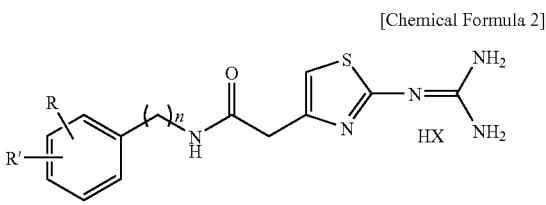

The synthesized compounds were summarized in following Table 1. In the table, hydrogen atom used as R and/or R' was not marked.

TABLE 1

| Compound No. | CODE | n | R and R' |
|---|---|---|---|
| 1 | KHG23168 | 0 | 2-F, 5-NO$_2$ |
| 2 | KHG23169 | 0 | 2-Cl, 4-F |
| 3 | KHG23170 | 0 | 3-Cl, 4-Me |
| 4 | KHG23171 | 0 | 4-F |
| 5 | KHG23172 | 0 | 2-F, 5-Cl |
| 6 | KHG23173 | 0 | 2-F, 4-Cl |
| 7 | KHG23174 | 0 | 2-Cl, 4-Me |
| 8 | KHG23175 | 0 | 4-Me |
| 9 | KHG23176 | 0 | 4-CN |
| 10 | KHG23177 | 0 | |
| 11 | KHG23178 | 0 | 4-Br |
| 12 | KHG23179 | 0 | 3-F, 4-OMe |
| 13 | KHG23184 | 0 | 4-Cl |
| 14 | KHG23185 | 0 | 3-Cl, 5-Cl |
| 15 | KHG23185 | 0 | 3,-Cl, 5-Cl |
| 16 | KHG23186 | 0 | 4-Et |
| 17 | KHG23187 | 1 | 4-Me |
| 18 | KHG23188 | 2 | 4-Me |
| 19 | KHG23189 | 1 | 3-F, 4-F |
| 20 | KHG23190 | 2 | 4-F |
| 21 | KHG23191 | 0 | 2-Br, 4-Me |
| 22 | KHG23192 | 0 | 4-OEt |
| 23 | KHG23379 | 0 | 4-iPr |
| 24 | KHG23380 | 0 | 4-NO$_2$ |
| 25 | KHG23381 | 0 | 4-Decyl |
| 26 | KHG23382 | 0 | 3-CO$_2$Et |
| 27 | KHG23383 | 0 | 4-nHexyl |
| 28 | KHG23384 | 0 | 4-n-BuO |
| 29 | KHG23385 | 0 | 4-CO$_2$Et |
| 30 | KHG23386 | 0 | 4-n-Heptyl |
| 31 | KHG23387 | 0 | 4-CH$_2$CN |
| 32 | KHG23388 | 0 | 4-n-Bu |
| 33 | KHG23389 | 0 | 4-OPh |
| 34 | KHG23391 | 0 | 2-Cl, 6-Cl, 4-CF$_3$ |
| 35 | KHG23392 | 0 | 2-F, 3-F, 4-F |
| 36 | KHG23393 | 0 | 2-Me, 4-OMe |
| 37 | KHG23394 | 0 | 3-CF$_3$, 5-CF$_3$ |
| 38 | KHG23395 | 0 | 2-Cl, 3-Cl, 5-Cl, 6-Cl, |
| 39 | KHG23397 | 0 | 3-Cl, 4-Me |
| 40 | KHG23398 | 0 | 2-Cl, 6-Cl, 4-CF$_3$O |
| 41 | KHG23399 | 0 | 3-F, 4-MeO |

Synthesis of Compound KHG23168

[2-(2-(diaminomethyleneamino)thiazole-4-yl)-N-(2-fluoro-5-nitrophenyl)acetamide hydrochloride] [n=0, (R, R'; containing benzyl group, identical thereafter)=C$_6$H$_3$(2-F, 5-NO$_2$)]

The compound was synthesized by conducting the reaction of following Reaction Formula 1:

[Reaction Formula 1]

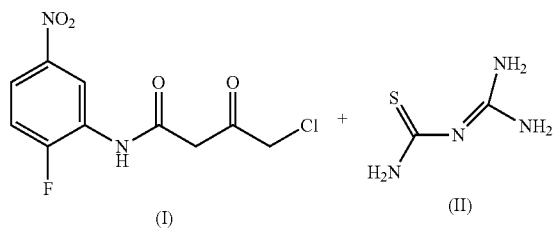

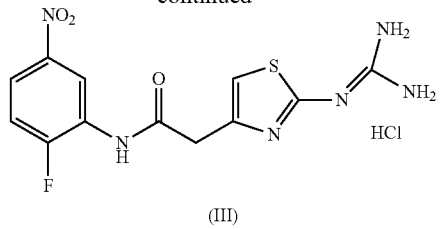

0.549 g of Compound I [4-chloro-N-(2-fluoro-5-nitrophenyl)-3-oxobutyramide, 0.002 mol] was dissolved in 5 mL of ethanol. Then, 0.236 g of Compound II (guanylthiourea, 0.002 mol) was added hereto, and heated to reflux for 2 hours. The obtained reaction mixture was cooled to room temperature, and then the suitable amount of ethylether was added to crystallize, generating precipitation within 12 hours. The precipitation was filtrated to obtain white crystalline solid III (0.648 g).

yield: 86%, melting point: 248.4-250.1° C.
$^1$H NMR (300 MHz, DMSO-d$_6$) δ 3.88 (s, 2H, 4-CH$_2$), 7.16 (s, 1H, vinyl-H), 7.58 (app. t, 1H, J=9.5 Hz, ArH), 8.05 (ddd, 1H, J=9.1 Hz, ArH), 8.28 (br. s, 3H, NH), 8.95 (dd, 1H, J=6.7, 2.9 Hz, ArH), 10.45 (s, 1H, amide NH), 12.23 (br. s, 1H, NH).

Hereinafter, following compounds were synthesized by the same method as above, except that the starting materials were suitably selected according to the final products.

KHG23169

N-(2-chloro-4-fluorophenyl)-2-(2-(diaminomethyleneamino)thiazole-4-yl)acetamide hydrochloride [n=0, (R, R')=C$_6$H$_3$(2-Cl, 4-F)]

yield: 70%, melting point: 232.8-233.9° C.
$^1$H NMR (300 MHz, DMSO-d$_6$) δ 3.78 (s, 2H, 4-CH$_2$), 7.15 (s, 1H, vinyl-H), 7.22 (td, 1H, J=8.5, 2.9 Hz, ArH), 7.51 (dd, 1H, J=8.6, 2.9 Hz, ArH), 7.65 (dd, 1H, J=8.9, 5.9 Hz, ArH), 8.32 (br. s, 3H, NH), 9.82 (s, 1H, amide, NH), 12.33 (br. s, 1H, NH).

KHG23170

N-(3-chloro-4-methylphenyl)-2-(2-(diaminomethyleneamino)thiazole-4-yl)acetamide hydrochloride [n=0, (R, R')=C$_6$H$_3$(3-Cl, 4-CH$_3$)]

yield: 63%, melting point: 238.6-240.4° C.
$^1$H NMR (300 MHz, DMSO-d$_6$) δ 2.26 (s, 3H, 4-CH$_3$), 3.72 (s, 2H, 4-CH$_2$), 7.13 (s, 1H, vinyl-H), 7.26 (d, 2H, J=8.4 Hz, ArH), 7.38 (dd, 2H, J=8.3, 2.0 Hz, ArH), 7.80 (d, 1H, J=1.9 Hz, ArH), 8.30 (br. s, 3H, NH), 10.43 (s, 1H, amide, NH), 12.30 (br. s, 1H, NH).

KHG23171

2-(2-(diaminomethyleneamino)thiazole-4-yl)-N-(4-fluorophenyl)acetamide hydrochloride [n=0, (R, R')=C$_6$H$_4$(4-F)]

yield: 58%, melting point: 207.3-208.2° C.
$^1$H NMR (300 MHz, DMSO-d$_6$) δ 3.72 (s, 2H, 4-CH$_2$), 7.12-7.18 (m, 3H, vinyl-H and ArH), 7.60-7.65 (m, 2H, ArH), 8.30 (br. s, 3H, NH), 10.35 (s, 1H, amide, NH), 12.25 (br. s, 1H, NH).

KHG23172

N-(5-chloro-2-fluorophenyl)-2-(2-(diaminomethyl-eneamino)thiazole-4-yl)acetamide hydrochloride [n=0, (R, R')=$C_6H_3$(2-F, 5-Cl)]

yield: 66%, melting point: 209.3-210.0° C.
$^1$H NMR (300 MHz, DMSO-$d_6$) δ 3.77 (s, 2H, 4-$CH_2$), 6.94 (s, 1H, vinyl-H), 6.94 (ddd, 1H, J=8.8, 4.2, 2.8 Hz, ArH), 7.33 (dd, 1H, J=10.5, 8.9 Hz, ArH), 7.86 (br. s, 3H, NH), 8.05 (dd, 1H, J=6.7, 2.6 Hz, ArH), 10.14 (s, 1H, amide, NH), 12.28 (br. s, 1H, NH).

KHG23173

N-(4-chloro-2-fluorophenyl)-2-(2-(diaminomethyl-eneamino)thiazole-4-yl)acetamide hydrochloride [n=0, (R, R')=$C_6H_3$(2-F, 4-Cl)]

yield: 68%, melting point: 237.2-239.8° C.
$^1$H NMR (300 MHz, DMSO-$d_6$) δ 3.80 (s, 2H, 4-$CH_2$), 7.13 (s, 1H, vinyl-H), 7.24-7.27 (m, 1H, ArH), 7.50 (dd, 1H, J=10.7, 2.3 Hz, ArH), 7.86-7.93 (m, 1H, ArH), 8.31 (br. s, 3H, NH), 10.10 (s, 1H, amide, NH), 12.35 (br. s, 1H, NH).

KHG23174

N-(2-chloro-4-methylphenyl)-2-(2-(diaminomethyl-eneamino)thiazole-4-yl)acetamide hydrochloride [n=0, (R, R')=$C_6H_3$(2-Cl, 4-$CH_3$)]

yield: 66%, melting point: 218.6-220.0° C.
$^1$H NMR (300 MHz, DMSO-$d_6$) δ 2.27 (s, 3H, 4-$CH_3$), 3.77 (s, 2H, 4-$CH_2$), 7.11-7.55 (m, 4H, vinyl-H and ArH), 8.32 (br. s, 3H, NH), 9.66 (s, 1H, amide, NH), 12.33 (br. s, 1H, NH).

KHG23175

2-(2-(diaminomethyleneamino)thiazole-4-yl)-N-p-tolylacetamide hydrochloride [n=0, (R, R')=$C_6H_4$(4-$CH_3$)]

yield: 68%, melting point: 236.2-238.3
$^1$H NMR (300 MHz, DMSO-$d_6$) δ 2.23 (s, 3H, 4-$CH_3$), 3.69 (s, 2H, 4-$CH_2$), 7.08-7.49 (m, 5H, vinyl-H and ArH), 8.29 (br. s, 3H, NH), 10.18 (s, 1H, amide, NH), 12.32 (br. s, 1H, NH).

KHG23176

N-(4-cyanophenyl)-2-(2-(diaminomethyleneamino)thiazole-4-yl)acetamide hydrochloride [n=0, (R, R')=$C_6H_4$(4-CN)]

yield: 78%, melting point: 218.4-219.4° C.
$^1$H NMR (300 MHz, DMSO-$d_6$) δ 3.80 (s, 2H, 4-$CH_2$), 7.16 (s, 1H, vinyl-H), 7.78 and 7.82 (AB pattern, 4H, $J_{AB}$=8.6 Hz, ArH), 8.31 (br. s, 3H, NH), 10.88 (s, 1H, amide, NH), 12.39 (br. s, 1H, NH).

KHG23177

2-(2-(diaminomethyleneamino)thiazole-4-yl)-N-phenylacetamide hydrochloride [n=0, (R, R')=$C_6H_5$]

yield: 62%, melting point: 197.8-198.1° C.
$^1$H NMR (300 MHz, DMSO-$d_6$) δ 3.72 (s, 2H, 4-$CH_2$), 7.04 (app. t, 1H, J=74 Hz, ArH), 7.12 (s, 1H, vinyl-H), 7.29 (app. t, 2H, J=7.9 Hz, ArH), 7.60 (d, 2H, H=7.7 Hz, ArH), 8.30 (br. s, 3H, NH), 10.27 (s, 1H, amide, NH), 12.30 (br. s, 1H, NH).

KHG23178

N-(4-bromophenyl)-2-(2-(diaminomethyleneamino)thiazole-4-yl)acetamide hydrochloride [n=0, (R, R')=$C_6H_4$(4-Br)]

yield: 79%, melting point: 246.4-247.0° C.
$^1$H NMR (300 MHz, DMSO-$d_6$) δ 3.73 (s, 2H, 4-$CH_2$), 7.12 (s, 1H, vinyl-H), 7.47-7.60 (m, 4H, ArH), 8.27 (br. s, 3H, NH), 10.44 (s, 1H, amide, NH), 12.26 (br. s, 1H, NH).

KHG23179

2-(2-(diaminomethyleneamino)thiazole-4-yl)-N-(3-fluoro-4-methoxyphenyl)acetamide hydrochloride [n=0, (R, R')=$C_6H_3$(3-F, 4-$OCH_3$)]

yield: 47%, melting point: 225.8-228.4° C.
$^1$H NMR (300 MHz, DMSO-$d_6$) δ 3.69 (s, 2H, 4-$CH_2$), 3.79 (s, 3H, 4-$OCH_3$), 7.07-7.61 (m, 4H, vinyl-H and ArH), 8.29 (br. s, 3H, NH), 10.38 (s, 1H, amide, NH), 12.38 (br. s, 1H, NH).

KHG23184

N-(4-chlorophenyl)-2-(2-(diaminomethyleneamino)thiazole-4-yl)acetamide hydrochloride [n=0, (R, R')=$C_6H_4$(4-Cl)]

yield: 68%, melting point: 244.3-245.0° C.
$^1$H NMR (300 MHz, DMSO-$d_6$) δ 3.73 (s, 2H, 4-$CH_2$), 7.14 (s, 1H, vinyl-H), 7.36 (d, 2H, J=8.8 Hz, ArH), 7.64 (d, 2H, J=8.8 Hz, ArH), 8.28 (br. s, 3H, NH), 10.42 (s, 1H, amide, NH), 12.20 (br. s, 1H, NH).

KHG23185

2-(2-(diaminomethyleneamino)thiazole-4-yl)-N-(3,5-dichlorophenyl)acetamide hydrochloride [n=0, (R, R')=$C_6H_3$(3-Cl, 5-Cl)]

yield: 91%, melting point: 248.5-249.2° C.
$^1$H NMR (300 MHz, DMSO-$d_6$) δ 3.77 (s, 2H, 4-$CH_2$), 7.16 (s, 1H, vinyl-H), 7.28 (t, 1H, J=1.8 Hz, ArH), 7.72 (d, 2H, J=1.8 Hz, ArH), 8.29 (br. s, 3H, NH), 10.84 (s, 1H, amide, NH), 12.35 (br. s, 1H, NH).

KHG23186

2-(2-(diaminomethyleneamino)thiazole-4-yl)-N-(4-ethylphenyl)acetamide hydrochloride [n=0, (R, R')=$C_6H_4$(4-$CH_2CH_3$)]

yield: 38%, melting point: 228.0-229.1° C.
$^1$H NMR (300 MHz, DMSO-$d_6$) δ 1.15 (t, 3H, J=7.6 Hz, 4-$CH_2CH_3$), 2.54 (q, 2H, H=7.6 Hz, 4-$CH_2CH_3$), 3.70 (s, 2H, 4-$CH_2$), 7.12 (s, 1H, vinyl-H), 7.13 (d, 2H, J=8.3 Hz, ArH), 7.50 (d, 2H, J=8.4 Hz, ArH), 8.29 (br. s, 3H, NH), 10.17 (s, 1H, amide, NH), 12.23 (br. s, 1H, NH).

KHG23187

2-(2-(diaminomethyleneamino)thiazole-4-yl)-N-(4-methylbenzyl)acetamide hydrochloride [n=1, (R, R')=C$_6$H$_4$(4-CH$_3$)]

yield: 44%, melting point: 187.9-188.6° C.
$^1$H NMR (300 MHz, DMSO-d$_6$) δ 2.27 (s, 3H, 4-CH$_3$), 3.54 (s, 2H, 4-CH$_2$), 4.23 (d, 2H, J=5.8 Hz, NHCH$_2$), 7.06 (s, 1H, vinyl-H), 7.12 (s, 4H, ArH), 8.31 (br. s, 3H, NH), 8.54 (t, 1H, J=5.8 Hz, NHCH$_2$), 12.35 (br. s, 1H, NH).

KHG23188

2-(2-(diaminomethyleneamino)thiazole-4-yl)-N-(4-methylphenethyl)acetamide hydrochloride [n=2, (R, R')=C$_6$H$_4$(4-CH$_3$)]

yield: 17%, melting point: 169.3-170.1° C.
$^1$H NMR (300 MHz, DMSO-d$_6$) δ 2.26 (s, 3H, 4-CH$_3$), 2.65 (t, 2H, J=6.9 Hz, —NHCH$_2$CH$_2$—), 3.24 (app. q, 2H, J=6.7 Hz, —NHCH$_2$CH$_2$—), 3.40 (s, 2H, 4-CH$_2$), 6.81 (s, 1H, vinyl-H), 7.03-7.09 (m, 4H, ArH), 7.90 (br. s, 4H, NH), 8.04 (br. t, 1H, J=5.5 Hz, —NHCH$_2$CH$_2$—), 12.25 (br. s, 1H, NH)

KHG23189

2-(2-(diaminomethyleneamino)thiazole-4-yl)-N-(3,4-difluorobenzyl)acetamide hydrochloride [n=1, (R, R')=C$_6$H$_3$(3-F,4-F)]

yield: 89%, melting point: 206.9-207.6° C.
$^1$H NMR (300 MHz, DMSO-d$_6$) δ 3.56 (s, 2H, 4-CH$_2$), 4.27 (d, 2H, J=6.0 Hz, NHCH$_2$), 7.08-7.42 (m, 4H, vinyl-H and ArH), 8.30 (br. s, 3H, NH), 8.67 (t, 1H, J=6.0 Hz, NHCH$_2$), 12.39 (br. s, 1H, NH).

KHG23190

2-(2-(diaminomethyleneamino)thiazole-4-yl)-N-(4-fluorophenethyl)acetamide hydrochloride [n=2, (R, R')=C$_6$H$_4$(4-F)]

yield: 91%, melting point:
$^1$H NMR (300 MHz, DMSO-d$_6$) δ 2.69 (app. t, 2H, J=7.2 Hz, NHCH$_2$CH$_2$), 3.27 (app. q, 2H, J=6.5 Hz, NHCH$_2$CH$_2$), 3.44 (s, 2H, 4-CH$_2$), 6.96 (s, 1H, vinyl-H), 7.05-7.23 (m, 4H, ArH), 8.13 (t, 1H, J=5.4 Hz, NHCH$_2$CH$_2$), 8.25 (br. s, 3H, NH), 12.39 (br. s, 1H, NH).

KHG23191

N-(2-bromo-4-methylphenyl)-2-(2-(diaminomethyleneamino)thiazole-4-yl)acetamide hydrochloride [n=0, (R, R')=C$_6$H$_3$(2-Br, 4-CH$_3$)]

yield: 47%, melting point: 219.7-220.5° C.
$^1$H NMR (300 MHz, DMSO-d$_6$) δ 2.28 (s, 3H, 4-CH$_3$), 3.76 (s, 2H, 4-CH$_2$), 7.15-7.48 (m, 4H, vinyl-H and ArH), 8.34 (br. s, 3H, NH), 9.57 (s, 1H, amide NH), 12.47 (br. s, 1H, NH).

KHG23192

N-(4-ethoxyphenyl)-2-(2-(diaminomethyleneamino)thiazole-4-yl)acetamide hydrochloride [n=0, (R, R')=C$_6$H$_4$(4-OCH$_2$CH$_3$)]

yield: 78%, melting point: 242.1-242.6° C.
$^1$H NMR (300 MHz, DMSO-d$_6$) δ 1.30 (t, 3H, J=6.9 Hz, 4-OCH$_2$CH$_3$), 3.68 (s, 2H, 4-CH$_2$), 3.97 (q, 2H, J=6.9 Hz, 4-OCH$_2$CH$_3$), 6.84-6.87 (m, 2H, ArH), 7.10 (s, 1H, vinyl-H), 7.47-7.50 (m, 2H, ArH), 8.29 (br. s, 3H, NH), 10.09 (s, 1H, amide NH), 12.34 (br. s, 1H, NH).

KHG23379

2-(2-(diaminomethyleneamino)thiazole-4-yl)-N-(4-isopropylphenyl)acetamide hydrochloride [n=0, (R, R')=C$_6$H$_4${4-CH(CH$_3$)$_2$}]

yield: 42%, melting point: 220.0~223.0° C.
$^1$H NMR (300 MHz, DMSO-d$_6$) δ 10.21 (s, 1H, amide NH), 8.31 (br. s, 4H, NH), 7.51 (d, 2H, J=8.6 Hz, Ar—H), 7.16 (d, 2H, J=8.5 Hz, Ar—H), 7.11 (s, 1H, vinyl-H), 3.70 (s, 2H, CH2), 2.78 (m, 1H, J=6.8 Hz, CH(CH3)2), 1.18, 1.16 (2s, 6H, 2×CH3).

KHG23380

2-(2-(diaminomethyleneamino)thiazole-4-yl)-N-(4-nitrophenyl)acetamide hydrochloride [n=0, (R, R')=C$_6$H$_4$(4-NO$_2$)]

yield: 86%, melting point: 245.3~245.9° C.
$^1$H NMR (300 MHz, DMSO-d$_6$) δ 11.04 (s, 1H, amide NH), 8.28 (br. s, 4H, NH), 8.21 (d, 2H, J=9.2 Hz, Ar—H), 7.88 (d, 2H, J=9.2 Hz, Ar—H), 7.16 (s, 1H, vinyl-H), 3.83 (s, 2H, CH$_2$).

KHG23381

N-(4-decylphenyl)-2-(2-(diaminomethyleneamino)thiazole-4-yl)acetamide hydrochloride [n=0, (R, R')=C$_6$H$_4${4-(CH$_2$)$_9$CH$_3$}]

yield: 62%, melting point: 240.0~242.9° C.
$^1$H NMR (300 MHz, DMSO-d$_6$) δ 10.19 (s, 1H, amide NH), 8.31 (br. s, 4H, NH), 7.08~7.50 (m, 4H, Ar—H), 7.11 (s, 1H, vinyl-H), 3.70 (s, 2H, CH$_2$), 2.50 (m, 2H, —CH$_2$—), 1.51 (m, 2-H, —CH$_2$—), 1.23 (m, 14H, (CH$_2$)$_7$), 0.84 (t, 3H, J=6.6 Hz, CH$_3$).

KHG23382 ethyl 3-(2-(2-(diaminomethyleneamino)thiazole-4-yl)acetamido)benzoate hydrochloride [n=0, (R, R')=C$_6$H$_4$(3-COOCH$_2$CH$_3$)]

yield: 58%, melting point: 208.3~209.3° C.
$^1$H NMR (300 MHz, DMSO-d$_6$) δ 10.57 (s, 1H, amide NH), 8.30 (br. s, 4H, NH), 8.28 (m, 1H, Ar—H), 7.87 (d, 1H, J=8.1 Hz, Ar—H), 7.64 (app. d, 1H, J=7.7 Hz, Ar—H), 7.45 (t, 1H, J=7.9 Hz, Ar—H), 7.13 (s, 1H, vinyl-H), 4.31 (q, 2H, OCH$_2$CH$_3$), 3.76 (s, 2H, CH$_2$), 1.32 (t, 3H, OCH$_2$CH$_3$).

KHG23383

2-(2-(diaminomethyleneamino)thiazole-4-yl)-N-(4-hexylphenyl)acetamide hydrochloride [n=0, (R, R')=C$_6$H$_4${4-(CH$_2$)$_5$CH$_3$}]

yield: 65%, melting point: 245.4~246.4° C.
$^1$H NMR (300 MHz, DMSO-d$_6$) δ 10.14 (s, 1H, amide NH), 8.28 (br. s, 4H, NH), 7.48 (d, 2H, J=8.3 Hz, Ar—H), 7.11 (s, 1H, vinyl-H), 7.10 (d, 2H, J=8.3 Hz, Ar—H), 3.69 (s, 2H, CH$_2$), 2.50 (m, 2H, —CH$_2$—), 1.52 (m, 2-H, —CH$_2$—), 1.25 (m, 6H, (CH$_2$)$_3$), 0.84 (m, 3H, CH$_3$).

KHG23384

N-(4-butoxyphenyl)-2-(2-(diaminomethyleneamino) thiazole-4-yl)acetamide hydrochloride [n=0, (R, R')=C$_6$H$_4${4-O(CH$_2$)$_3$CH$_3$}]

yield: 66%, melting point: 243.2~244.3° C.
$^1$H NMR (300 MHz, DMSO-d$_6$) δ 10.13 (s, 1H, amide NH), 8.31 (br. s, 4H, NH), 7.49 (d, 1H, J=9.0 Hz, Ar—H), 7.09 (s, 1H, vinyl-H), 6.85 (d, 2H, J=8.9 Hz, Ar—H), 3.90 (t, 2H, J=6.4 Hz, OCH$_2$CH$_2$CH$_2$CH$_3$), 3.68 (s, 2H, CH$_2$), 1.66 (m, 2H, OCH$_2$CH$_2$CH$_2$CH$_3$), 1.41 (m, 2H, J=7.5 Hz, OCH$_2$CH$_2$CH$_2$CH$_3$), 0.91 (t, 3H, CH$_3$).

KHG23385 ethyl 4-(2-(2-(diaminomethyleneamino)thiazole-4-yl)acetamido)benzoate hydrochloride [n=0, (R, R')=C$_6$H$_4$(4-COOCH$_2$CH$_3$)]

yield: 62%, melting point: 219.5~220.5° C.
$^1$H NMR (300 MHz, DMSO-d$_6$) δ 10.73 (s, 1H, amide NH), 8.32 (br. s, 4H, NH), 7.91 (d, 2H, J=8.8 Hz, Ar—H), 7.76 (d, 2H, J=8.8 Hz, Ar—H), 7.15 (s, 1H, vinyl-H), 4.28 (q, 2H, J=7.0 Hz, OCH$_2$CH$_3$), 3.79 (s, 2H, CH$_2$), 1.30 (t, 3H, J=7.1 Hz, OCH$_2$CH$_3$).

KHG23386

2-(2-(diaminomethyleneamino)thiazole-4-yl)-N-(4-hexylphenyl)acetamide hydrochloride [n=0, (R, R')=C$_6$H$_4$(4-(CH$_2$)$_2$CH$_3$)]

yield: 73%, melting point: 246.6~247.1° C.
$^1$H NMR (300 MHz, DMSO-d$_6$) δ 10.17 (s, 1H, amide NH), 8.30 (br. s, 4H, NH), 7.48 (d, 2H, J=8.2 Hz, Ar—H), 7.11 (s, 1H, vinyl-H), 7.09 (d, 2H, J=8.4 Hz, Ar—H), 3.69 (s, 2H, CH$_2$), 2.52~2.43 (m, 2H, —CH$_2$—), 1.52 (quin, 2-H, J=6.8 Hz, —CH$_2$—), 1.24 (br. d, 8H, (CH$_2$)$_4$), 0.84 (m, 3H, J=6.7 Hz, CH$_3$).

KHG23387

N-(4-(cyanomethyl)phenyl)-2-(2-(diaminomethyleneamino)thiazole-4-yl)acetamide hydrochloride [n=0, (R, R')=C$_6$H$_4$(4-CH$_2$CN)]

yield: 81%, melting point: 237.1~238.2° C.
$^1$H NMR (300 MHz, DMSO-d$_6$) δ 10.38 (s, 1H, amide NH), 8.30 (br. s, 4H, NH), 7.63 (d, 2H, J=8.6 Hz, Ar—H), 7.19 (d, 2H, J=8.6 Hz, Ar—H), 7.12 (s, 1H, vinyl-H), 3.93 (s, 2H, CH2), 3.73 (s, 2H, CH$_2$).

KHG23388

N-(4-butylphenyl)-2-(2-(diaminomethyleneamino) thiazole-4-yl)acetamide hydrochloride [n=0, (R, R')=C$_6$H$_4${4-(CH$_2$)$_3$CH$_3$}]

yield: 70%, melting point: 243.9~244.7° C.
$^1$H NMR (300 MHz, DMSO-d$_6$) δ 10.19 (s, 1H, amide NH), 8.31 (br. s, 4H, NH), 7.49 (d, 2H, J=8.3 Hz, Ar—H), 7.11 (s, 1H, vinyl-H), 7.10 (d, 2H, J=7.2 Hz, Ar—H), 3.70 (s, 2H, CH$_2$), 2.53~2.49 (m, 2H, —CH$_2$—), 1.52 (m, 2-H, J=7.4 Hz, —CH$_2$—), 1.28 (m, 2H, J=7.3 Hz, —CH$_2$—), 0.88 (m, 3H, J=7.29 Hz, CH$_3$).

KHG23389

2-(2-(diaminomethyleneamino)thiazole-4-yl)-N-(4-phenoxyphenyl)acetamide hydrochloride [n=0, (R, R')=C$_6$H$_4${4-O(C$_6$H$_5$)}]

yield: 62%, melting point: 236.2~236.8° C.
$^1$H NMR (300 MHz, DMSO-d$_6$) δ 10.28 (s, 1H, amide NH), 8.28 (br. s, 4H, NH), 7.63~6.93 (m, 10H, Ar—H, vinyl-H), 3.71 (s, 2H, CH$_2$).

KHG23391

2-(2-(diaminomethyleneamino)thiazole-4-yl)-N-(2, 6-dichloro-4-(trifluoromethyl)phenyl)acetamide hydrochloride [n=0, (R, R')=C$_6$H$_2$(2-Cl,6-Cl,4-CF$_3$)]

yield: 71%, melting point: 293.8~302.3° C. (decomposition)
$^1$H NMR (300 MHz, DMSO-d$_6$) δ 10.38 (s, 1H, amide NH), 8.36 (br. s, 4H, NH), 7.98 (m, 2H, Ar—H), 7.17 (s, 1H, vinyl-H), 3.80 (s, 2H, CH$_2$).

KHG23392

2-(2-(diaminomethyleneamino)thiazole-4-yl)-N-(2,3, 4-trifluorophenyl)acetamide hydrochloride [n=0, (R, R')=C$_6$H$_2$(2-F, 3-F, 4-F)]

yield: 39%, melting point: 229.0~229.9° C.
$^1$H NMR (300 MHz, DMSO-d$_6$) δ 10.25 (s, 1H, amide NH), 8.33 (br. s, 4H, NH), 7.61~7.24 (m, 2H, Ar—H), 7.13 (s, 1H, vinyl-H), 3.80 (s, 2H, CH$_2$).

KHG23393

2-(2-(diaminomethyleneamino)thiazole-4-yl)-N-(4-methoxy-2-methylphenyl)acetamide hydrochloride [n=0, (R, R')=C$_6$H$_3$(2-Me,4-OMe)]

yield: 64%, melting point: 228.7~229.2° C.
$^1$H NMR (300 MHz, DMSO-d$_6$) δ 9.42 (s, 1H, amide NH), 8.30 (br. s, 4H, NH), 7.76 (m, 2H, J=8.5 Hz, Ar—H), 6.77 (s, 1H, vinyl-H), 6.72 (m, 1H, J=8.3 Hz, Ar—H), 3.71 (s, 3H, OCH$_3$), 3.68 (s, 2H, CH$_2$), 2.11 (s, 3H, CH$_3$).

KHG23394

N-(3,5-bis(trifluoromethyl)phenyl)-2-(2-(diaminomethyleneamino)thiazole-4-yl)acetamide hydrochloride [n=0, (R, R')=C$_6$H$_3${3,5-(CF$_3$)$_2$}]

yield: 77%, melting point: 186.6~187.6° C.
$^1$H NMR (300 MHz, DMSO-d$_6$) δ 11.17 (br. s, 1H, amide NH), 8.33 (s, 2H, Ar—H), 8.25 (br. s, 4H, NH), 7.76 (s, 1H, Ar—H), 7.17 (s, 1H, vinyl-H), 3.82 (s, 2H, CH$_2$).

KHG23395

2-(2-(diaminomethyleneamino)thiazole-4-yl)-N-(2,3, 5,6-tetrachlorophenyl)acetamide hydrochloride [n=0, (R, R')=C$_6$H$_1$(2-Cl, 3-Cl, 5-Cl, 6-Cl)]

yield: 74%, melting point: 293.8~302.3° C. (decomposition)

$^1$H NMR (300 MHz, DMSO-d$_6$) δ 1041 (s, 1H, amide NH), 8.30 (br. s, 4H, NH), 8.11 (s, 1H, Ar—H), 7.16 (s, 1H, vinyl-H), 3.79 (s, 2H, CH$_2$).

KHG23397

N-(3-chloro-4-methylphenyl)-2-(2-(diaminomethyleneamino)thiazole-4-yl)acetamide hydrochloride [n=0, (R, R')=C$_6$H$_3$(3-Cl,4-Me)]

yield: 67%, melting point: 247.4~247.9° C.
$^1$H NMR (300 MHz, DMSO-d$_6$) δ 10.49 (s, 1H, amide NH), 8.31 (br. s, 4H, NH), 7.81 (d, 1H, J=2.0 Hz, Ar—H), 7.41 (dd, 1H, J=8.2, 2.1 Hz, Ar—H), 7.26 (d, 1H, J=8.2 Hz, Ar—H), 7.13 (s, 1H, vinyl-H), 3.73 (s, 3H, OCH$_3$), 2.26 (s, 3H, OCH$_3$).

KHG23398

2-(2-(diaminomethyleneamino)thiazole-4-yl)-N-(2,6-dichloro-4-(trifluoromethoxy)phenyl)acetamide hydrochloride [n=0, (R, R')=C$_6$H$_2$(2,6-Cl$_2$,4-OCF$_3$)]

yield: 74%, melting point: 293.8~302.3° C. (decomposition)
$^1$H NMR (300 MHz, DMSO-d$_6$) δ 1041 (s, 1H, amide NH), 8.30 (br. s, 4H, NH), 8.11 (s, 1H, Ar—H), 7.16 (s, 1H, vinyl-H), 3.79 (s, 2H, CH$_2$).

KHG23399

2-(2-(diaminomethyleneamino)thiazole-4-yl)-N-(3-fluoro-4-methoxyphenyl)acetamide hydrochloride [n=0, (R, R')=C$_6$H$_3$(3-F,4-OMe)]

yield: 58%, melting point: 235.7~237.0° C.
$^1$H NMR (300 MHz, DMSO-d$_6$) δ 9.82 (s, 1H, amide NH), 8.33 (br. s, 4H, NH), 7.65 (t, 1H, J=8.2 Hz, Ar—H), 7.10 (d, 1H, J=6.4 Hz, Ar—H), 7.05 (s, 1H, vinyl-H), 6.95 (d, 1H, J=8.0 Hz, Ar—H), 3.76 (s, 3H, OCH$_3$), 2.27 (s, 3H, OCH$_3$).

Example 2

Synthesis of the Compound of Chemical Formula 3

The compound of following Chemical Formula 3 was synthesized:

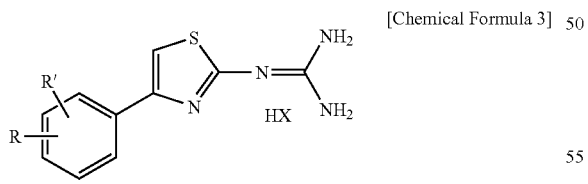

[Chemical Formula 3]

The synthesized compounds were summarized in following Table 2. In the table, hydrogen atom used as R and/or R' was not marked.

TABLE 2

|  | CODE | R and R' | HX |
|---|---|---|---|
| 1 | KHG24022 | 3-[O(CO)NH]-4 | HCl |
| 2 | KHG24024 | 4-Cl | HCl |

TABLE 2-continued

|  | CODE | R and R' | HX |
|---|---|---|---|
| 3 | KHG24025 | 4-F | HCl |
| 4 | KHG24026 | 2-F, 4-F | HCl |
| 5 | KHG24037 | 3-[OCH$_2$C(O)NH]-4 | HCl |
| 6 | KHG24038 | 4-Ph | HCl |
| 7 | KHG24039 | 3-(CHCHCHCH)-4 | HCl |
| 8 | KHG24040 | 4-Me | HBr |
| 9 | KHG24041 | 4-OMe | HBr |
| 10 | KHG24373 | 2-Cl | HBr |
| 11 | KHG24374 | 2-MeO | HBr |
| 12 | KHG24375 | 4-NO$_2$ | HBr |
| 13 | KHG24376 | 2-OMe, 4-OMe | HBr |
| 14 | KHG24377 | 2-F, 4-MeO | HBr |
| 15 | KHG24379 | 2-Cl, 4-Cl | HBr |
| 16 | KHG24380 |  | HBr |
| 17 | KHG24381 | 4-Br | HBr |
| 18 | KHG24382 | 3-Me | HBr |
| 19 | KHG24383 | 3-F | HBr |
| 20 | KHG24384 | 2-F | HBr |
| 23 | KHG24385 | 3-CF$_3$ | HBr |
| 24 | KHG24386 | 3-Br | HBr |
| 25 | KHG24387 | 4-Et | HBr |
| 26 | KHG24388 | 3-Cl | HBr |
| 27 | KHG24389 | 3-NO$_2$ | HBr |
| 28 | KHG24390 | 3-Cl, 4-Cl | HBr |
| 28 | KHG24391 | 2-F, 5-F | HBr |
| 30 | KHG24392 | 3-CF$_3$, 5-CF$_3$ | HBr |

KHG24022

2-(4-(2-oxo-2,3-dihydrobenzo[d]oxazole-6-yl)thiazole-2-yl)guanidine hydrochloride [(R, R')=3-[O(CO)NH]-4, HX=HCl]

The compound was synthesized by conducting the reaction of following Reaction Formula 2:

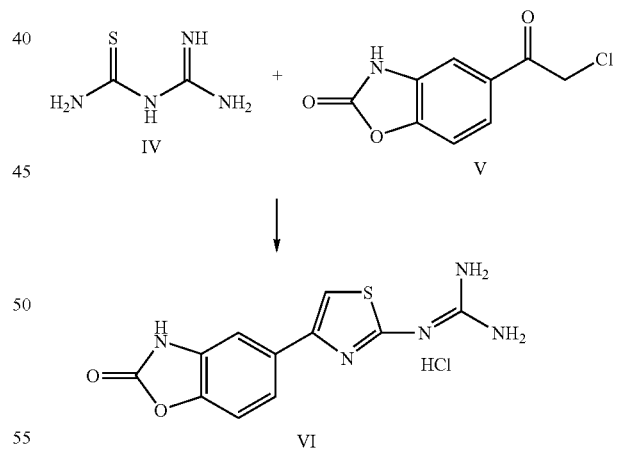

[Reaction Formula 2]

Guanylthiourea IV (1.69 mmol) and 5-chloroacetyl-2-benzoxazolinone V (1.69 mmol) were heated to reflux for 4 hours under ethanol solvent. Then, the reaction mixture was left at room temperature for 1 hour to generate solid. The obtained solid was filtrated to obtain thiazole-based compound VI.
yield: 74%, melting point: 313.7° C.
1H NMR (400 MHz, DMSO-d6) δ 11.78 (br. s, 1H, benzoxazol NH), 8.20 (br. s, 4H, NH), 7.92 (d, 1H, J=1.2 Hz, Ar—H), 7.75 (dd, 1H, J=8.2, 1.5 Hz, Ar—H), 7.11 (d, 1H, J=8.2 Hz, Ar—H).

Hereinafter, following compounds were synthesized by the same method as above, except that the starting materials were suitably selected according to the final products.

KHG24023

2-(5-(4-fluorobenzyl)-4-methylthiazole-2-yl)guanidine hydrochloride [(R, R')=4-F, HX=HCl]

yield: 66%, melting point: 245.6° C.
1H NMR (400 MHz, DMSO-d6) δ 10.17 (s, 1H, amide NH), 8.34 (br. s, 4H, NH), 7.68~7.64 (m, 2H, Ar—H), 7.20~7.64 (t, 2H, Ar—H), 2.49 (s, 3H, CH$_3$).

KHG24024

2-(4-(4-chlorophenyl)thiazole-2-yl)guanidine hydrochloride [(R, R')=4-Cl, HX=HCl]

yield: 75%, melting point: 264.9° C.
1H NMR (400 MHz, DMSO-d6) δ 8.33 (br. s, 4H, NH), 8.00 (d, 2H, J=8.5 Hz, Ar—H), 7.82 (s, 1H, Vinyl-H), 7.48 (d, 2H, J=8.5 Hz, Ar—H).

KHG24025

2-(4-(4-fluorophenyl)thiazole-2-yl)guanidine hydrochloride [(R, R')=4-F, HX=HCl]

yield: 69%, melting point: 223.3° C.
1H NMR (400 MHz, DMSO-d6) δ 8.32 (br. s, 4H, NH), 8.03~7.97 (m, 2H, Ar—H), 7.74 (s, 1H, Vinyl-H), 7.28~7.22 (m, 2H, Ar—H).

KHG24026

2-(4-(2,4-difluorophenyl)thiazole-2-yl)guanidine hydrochloride [(R, R')=2-F, 4-F, HX=HCl]

yield: 66%, melting point: 248.9° C.
1H NMR (400 MHz, DMSO-d6) δ 8.35 (br. s, 4H, NH), 8.24~8.16 (m, 2H, Ar—H), 7.60 (s, 1H, Vinyl-H), 7.42~7.13 (m, 2H, Ar—H), 7.19~7.13 (m, 1H, Ar—H).

KHG24037

2-(4-(3-oxo-3,4-dihydro-2H-benzo[b][1,4]oxazine-7-yl)thiazole-2-yl)guanidine hydrochloride

[(R, R')=3-[OCH$_2$C(O)NH]-4, HX=HCl]

yield: 91%, melting point: 233.3° C.
1H NMR (400 MHz, DMSO-d6) δ 10.75 (s, 1H, benzoxazin NH) 8.36 (br. s, 4H, NH), 7.52~6.97 (m, 5H, Ar—H), 4.60 (s, 1H, Vinyl-H).

KHG24038

2-(4-(biphenyl-4-yl)thiazole-2-yl)guanidine hydrochloride [(R, R')=4-Ph, HX=HCl]

yield: 91%, melting point: 300.3° C.
1H NMR (400 MHz, DMSO-d6) δ 8.23 (br. s, 4H, NH), 8.05~8.03 (m, 2H, Ar—H), 7.85 (s, 1H, Vinyl-H), 7.76~7.71 (m, 4H, Ar—H), 7.51~7.37 (m, 3H, Ar—H).

KHG24039

2-(4-(naphthalene-2-yl)thiazole-2-yl)guanidine hydrochloride [(R, R')=3-(CHCHCHCH)-4, HX=HCl]

yield: 91%, melting point: 263.2° C.
1H NMR (400 MHz, DMSO-d6) δ 8.54~8.53 (m, 1H, Ar—H), 8.28 (br. s, 4H, NH), 8.06~7.93 (m, 4H, Ar—H), 7.92 (s, 1H, Vinyl-H), 7.54~7.49 (m, 3H, Ar—H).

KHG24040

2-(4-p-tolylthiazole-2-yl)guanidine hydrobromide [(R, R')=4-CH3, HX=HBr]

yield: 86.6%, melting point: 281~284° C.
1H NMR (300 MHz, DMSO-d6) δ 8.17 (br-s, 4H, guanyl-NH), 7.86 (d, 2H, J=8.7 Hz, Ar—H), 7.6 (s, 1H, vinyl-H)), 6.99 (d, 2H, J=8.8 Hz, Ar—H), 3.79 (s, 3H, CH$_3$)

KHG24041

2-(4-(4-methoxyphenyl)thiazole-2-yl)guanidine hydrobromide [(R, R')=4-OCH3, HX=HBr]

yield: 83.6%, melting point: 225~227° C.
1H NMR (300 MHz, DMSO-d6) δ 8.18 (br-s, 4H, guanyl-NH), 7.82 (d, 2H, J=8.0 Hz, Ar—H), 7.7 (s, 1H, vinyl-H)), 7.24 (d, 2H, J=8.0 Hz, Ar—H), 2.33 (s, 3H, CH$_3$)

KHG 24373

2-(4-(2-chlorophenyl)thiazole-2-yl)guanidine hydrobromide [(R, R')=2-Cl, HX=HBr]

yield: 70.4%, melting point: 211.9° C.
1H NMR (300 MHz, DMSO-d6) δ 12.00 (s, 1H, HBr) 8.23 (s, 4H, (NH$_2$)$_2$) 7.87~7.84 (m, 1H, J=2.3 Hz, Ar—H) 7.76 (s, 1H, Vinyl-H) 7.60~7.57 (m, 1H, J=2.3 Hz, Ar—H) 7.48~7.42 (m, 2H, J=3.7 Hz, Ar—H).

KHG 24374

2-(4-(2-methoxyphenyl)thiazole-2-yl)guanidine hydrobromide [(R, R')=2-OCH$_3$, HX=HBr]

yield: 89.3% melting point: 245.4° C.
1H NMR (300 MHz, DMSO-d6) δ 8.17 (s, 4H, (NH$_2$)$_2$) 8.01 (d, 1H, J=6.6 Hz, Ar—H) 7.78 (s, 1H, Vinyl-H) 7.36 (t, 1H, J=6.6 Hz, Ar—H) 7.15 (d, 1H, J=7.8 Hz, Ar—H) 7.04 (t, 1H, J=7.1 Hz, Ar—H) 3.92 (s, 3H, OCH3).

KHG 24375

2-(4-(4-nitrophenyl)thiazole-2-yl)guanidine hydrobromide [(R, R')=4-NO$_2$, HX=HBr]

yield: 98%, melting point: 250.8° C.
1H NMR (300 MHz, DMSO-d6) δ 8.26 (d, 4H, J=3.7 Hz, Ar—H) 8.20 (s, 4H, (NH$_2$)$_2$) 8.14 (s, 1H, Vinyl-H).

KHG 24376

2-(4-(2,4-dimethoxyphenyl)thiazole-2-yl)guanidine hydrobromide [(R, R')=2-OCH$_3$, 4-OCH$_3$, HX=HBr]

yield: 81.3%, melting point: 213.0° C.

1H NMR (300 MHz, DMSO-d6) δ 11.82 (s, 1H, HBr) 8.17 (s, 4H, (NH$_2$)$_2$) 7.93 (d, 1H, J=8.6 Hz, Ar—H) 7.59 (s, 1H, Vinyl-H) 6.69 (s, 1H, Ar—H) 6.59 (d, 1H, J=8.6 Hz, Ar—H) 3.91 (s, 3H, OCH3) Hz, Ar—H) 3.81 (s, 3H, OCH3).

KHG 24377

2-(4-(2-fluoro-4-methoxyphenyl)thiazole-2-yl)guanidine hydrobromide [(R, R')=2-F, 4-OCH$_3$, HX=HBr]

yield: 36.8%, melting point: 202.6° C.
1H NMR (300 MHz, DMSO-d6) δ 8.21 (s, 4H, (NH$_2$)$_2$) 8.00 (t, 1H, J=9.0 Hz, Ar—H) 7.50 (s, 1H, Vinyl-H) 6.96 (d, 1H, J=11.3 Hz, Ar—H) 6.86 (d, 1H, J=6.3 Hz, Ar—H) 3.82 (s, 3H, OCH3).

HG 24379

2-(4-(2,4-dichlorophenyl)thiazole-2-yl)guanidine hydrobromide [(R, R')=2-Cl, 4-Cl, HX=HBr]

yield: 74.5%, melting point: 173.0° C.
1H NMR (300 MHz, DMSO-d6) δ 12.71 (s, 1H, HBr) 8.34 (s, 4H, (NH$_2$)$_2$) 7.92 (d, 1H, J=8.8 Hz, Ar—H) 7.80 (s, 1H, Vinyl-H) 7.74 (s, 1H, Ar—H) 7.50 (d, 1H, J=8.5 Hz, Ar—H).

KHG 24380

2-(4-phenylthiazole-2-yl)guanidine hydrobromide [(R, R')=H, HX=HBr]

yield: 79%, melting point: 209.5° C.
1H NMR (300 MHz, DMSO-d6) δ 11.96 (s, 1H, HBr) 8.22 (s, 4H, (NH$_2$)$_2$) 7.93 (d, 2H, J=7.1 Hz, Ar—H) 7.79 (s, 1H, Vinyl-H) 7.44 (t, 2H, J=7.3 Hz, Ar—H) 7.35 (t, 1H, J=7.3 Hz, Ar—H).

KHG 24381

2-(4-(4-bromophenyl)thiazole-2-yl)guanidine hydrobromide [(R, R')=4-Br, HX=HBr]

yield: 40%, melting point: 278.5° C.
1H NMR (300 MHz, DMSO-d6) δ 11.97 (s, 1H, HBr) 8.20 (s, 4H, (NH$_2$)$_2$) 7.92 (d, 2H, J=8.6 Hz, Ar—H) 7.87 (s, 1H, Vinyl-H) 7.62 (d, 2H, J=8.6 Hz, Ar—H).

KHG 24382

2-(4-m-tolylthiazole-2-yl)guanidine hydrobromide [(R, R')=3-CH$_3$, HX=HBr]

yield: 68%, melting point: 232.4° C.
1H NMR (300 MHz, DMSO-d6) δ 11.93 (s, 1H, HBr) 8.22 (s, 4H, (NH$_2$)$_2$) 7.75 (d, 2H, J=3.6 Hz, Ar—H) 7.71 (s, 1H, Vinyl-H) 7.33 (t, 1H, J=7.6 Hz, Ar—H) 7.17 (t, 1H, J=7.4 Hz, Ar—H) 2.36 (s, 3H, CH3).

KHG 24383

2-(4-(3-fluorophenyl)thiazole-2-yl)guanidine hydrobromide (R, R')=3-F, HX=HBr]

yield: 63.1%, melting point: 242.1° C. 1H NMR (300 MHz, DMSO-d6) δ 11.97 (s, 1H, HBr) 8.17 (s, 4H, (NH$_2$)$_2$) 7.92 (s, 1H, Vinyl-H) 7.86~7.80 (m, 2H, J=8.3 Hz, Ar—H) 7.50 (q, 1H, J=7.5 Hz, Ar—H) 7.20 (t, 1H, J=9.1 Hz, Ar—H).

KHG 24384

2-(4-(2-fluorophenyl)thiazole-2-yl)guanidine hydrobromide [(R, R')=2-F, HX=HBr]

yield: 68.9%, melting point: 229.6° C.
1H NMR (300 MHz, DMSO-d6) δ 11.97 (s, 1H, HBr) 8.23 (s, 4H, (NH$_2$)$_2$) 8.10 (t, 2H, J=7.9 Hz, Ar—H) 7.67 (s, 1H, Vinyl-H) 7.44~7.28 (m, 3H, Ar—H).

KHG 24385

2-(4-(3-(trifluoromethyl)phenyl)thiazole-2-yl)guanidine hydrobromide [(R, R')=3-CF$_3$, HX=HBr]

yield: 77.7%, melting point: 224.8° C.
1H NMR (300 MHz, DMSO-d6) δ 8.28 (m, 2H, J=6.1 Hz, Ar—H) 8.23 (s, 4H, (NH$_2$)$_2$) 8.07 (s, 1H, Vinyl-H) 7.70 (m, 2H, J=8.2 Hz, Ar—H).

KHG 24386

2-(4-(3-bromophenyl)thiazole-2-yl)guanidine hydrobromide [(R, R')=3-Br, HX=HBr]

yield: 77.9%, melting point: 179.8° C.
1H NMR (300 MHz, DMSO-d6) δ 8.21 (s, 4H, (NH$_2$)$_2$) 8.16 (s, 1H, Ar—H) 7.99 (s, 1H, Vinyl-H) 7.95 (d, 1H, J=5.3 Hz, Ar—H) 7.57 (d, 1H, J=7.1 Hz, Ar—H) 7.40 (t, 1H, J=7.9 Hz, Ar—H).

KHG 24387

2-(4-(4-ethylphenyl)thiazole-2-yl)guanidine hydrobromide [(R, R')=4-C$_2$H$_5$, HX=HBr]

yield: 55.4%, melting point: 234.8° C.
1H NMR (300 MHz, DMSO-d6) δ 11.97 (s, 1H, HBr) 8.25 (s, 4H, (NH$_2$)$_2$) 7.83 (d, 2H, J=8.2 Hz, Ar—H) 7.71 (s, 1H, Vinyl-H) 7.26 (d, 2H, J=8.2 Hz, Ar—H) 2.63 (q, 2H, J=7.6 Hz, CH2CH3) 1.18 (t, 3H, J=8.2 Hz, Ar—H).

KHG 24388

2-(4-(3-chlorophenyl)thiazole-2-yl)guanidine hydrobromide [(R, R')=3-Cl, HX=HBr]

yield: 63.6%, melting point: 210.4° C.
1H NMR (300 MHz, DMSO-d6) δ 8.21 (s, 4H, (NH$_2$)$_2$) 8.03 (s, 1H, Ar—H) 7.94 (s, 1H, Vinyl-H) 7.92 (m, 1H, Ar—H) 7.49~7.39 (m, 2H, Ar—H).

KHG 24389

2-(4-(4-nitrophenyl)thiazole-2-yl)guanidine hydrobromide [(R, R')=4-NO$_2$, HX=HBr]

yield: 89.5%, melting point: 237.8° C.
1H NMR (300 MHz, DMSO-d6) δ 11.97 (s, 1H, HBr) 8.69 (s, 1H, Ar—H) 8.43 (d, 2H, J=8.2 Hz, Ar—H) 8.22 (s, 4H, (NH$_2$)$_2$) 8.19 (m, 1H, Ar—H) 8.12 (s, 1H, Vinyl-H) 7.74 (t, 1H, J=8.0 Hz, Ar—H).

KHG 24390

2-(4-(3,4-dichlorophenyl)thiazole-2-yl)guanidine hydrobromide [(R, R')=3-Cl, 4-Cl, HX=HBr]

yield: 66.2%, melting point: 256.3° C.
1H NMR (300 MHz, DMSO-d6) δ 11.95 (s, 1H, HBr) 8.25 (s, 1H, Ar—H) 8.17 (s, 4H, $(NH_2)_2$) 7.99 (s, 1H, Vinyl-H) 7.95 (d, 1H, J=6.4 Hz, Ar—H) 7.68 (d, 1H, J=8.5 Hz, Ar—H).

KHG 24391

2-(4-(2,5-difluorophenyl)thiazole-2-yl)guanidine hydrobromide [(R, R')=2-F, 5-F, HX=HBr]

yield: 79%, melting point: 252.1° C.
1H NMR (300 MHz, DMSO-d6) δ 11.99 (s, 1H, HBr) 8.18 (s, 4H, $(NH_2)_2$) 8.00~7.95 (m, 1H, Ar—H) 7.75 (s, 1H, Vinyl-H) 7.44~7.35 (m, 1H, Ar—H) 7.30~7.22 (m, 2H, Ar—H).

KHG 24392

2-(4-(3,5-bis(trifluoromethyl)phenyl)thiazole-2-yl) guanidine hydrobromide [(R, R')=3-$CF_3$, 5-$CF_3$, HX=HBr]

yield: 27.6%, melting point: 265.6° C.
1H NMR (300 MHz, DMSO-d6) δ 8.60 (s, 2H, Ar—H) 8.32 (s, 1H, Ar—H) 8.21 (s, 4H, $(NH_2)_2$) 8.01 (s, 1H, Vinyl-H)

Experimental Example

Assay for Inhibiting Activity Against T-Type Calcium Channel

In the present invention, in order to search an efficient inhibitor against T-type calcium channel, a primary assay for T-type calcium channel inhibiting activity was conducted by a high-efficient assay using FDSS6000, wherein mammal HEK293 cell lines (originated from human kidney carcinoma cells) which specifically expresses α1G of T-type calcium channel was used for primary assay. Through the primary assay, compounds which show meaningful inhibition effects were selected. The selected compounds were used in a second assay for T-type calcium channel inhibiting activity using electrophysiological whole cell patch clamp method, wherein mammal HEK293 cell lines (originated from human kidney carcinoma cells) which specifically expresses $α_{1G}$ of T-type calcium channel was used for the second assay. As a reference drug, mibefradil which had been developed as T-type calcium channel inhibitor was used.

Experimental Example 1

Method of Assay for % Inhibiting Activity Against T-Type Calcium Channel Using FDSS6000

At 12-24 hours before being used for this assay, cells of HEK293 cell line ($α_{1G}$ cell line: KCTC 10519BP, Korean Collection for Type Cultures), which stably express $α_{1G}$ T-type calcium channel and Kir2.1, were sub-cultured in a poly-L-lysine treated 96-well plate with the density of $4×10^4$ per a well using a 96-well cell dispenser (Titertek). On the of assay, the 96-well plate to which the cells were attached were washed three times with HEPES buffer solution (150 mM of NaCl, 5 mM of KCl, 1 mM of $MgCl_2$, 2 mM of $CaCl_2$, 10 mM of HEPES, 10 mM of glucose; pH 7.4) using a 96-well plate automatic washing device (Bio Tek), then reacted with HEPES buffer solution containing 5 μM fluo-3/AM and 0.001% Pluronic F-127 under room temperature for 1 hour, to label with fluorescent dye, and then further washed two times with HEPES buffer solution.

Thereafter, at 10 minutes before the measurement using device FDSS6000, a washing with HEPES buffer solution containing 10 mM $CaCl_2$ was conducted once more, and the final volume was adjusted to 81 μl. Besides the above 96-well plate containing the cells, additional two drug 96-well plates were provided, wherein the 96-well plates contain inhibiting drug and KCl (final concentration: 75 mM) for activating T-type calcium channel, respectively. Since most of cell-based HTS devices are equipped with a liquid application system for injection of drug, but have no liquid sucking system, the inhibiting drug to be tested and KCl were respectively provided at the five-times higher concentration in 10 mM $CaCl_2$ HEPES buffer solution at the amount of 27 μl, diluted five-times at the final cell plate volume of 135 μl, and then used in this test. The concrete method of measurement using FDSS6000 was as follows: After recording the reference value of 20 seconds, the change of intracellular $Ca^{2+}$ concentration which induced by treatment of the inhibiting drug to be tested for 75 seconds followed by administration of KCl was measured, wherein the percentage (%) inhibition effect of the test drug, through estimating the area of ratio value of 340/380 in the control without treatment of the test drug as 100%. As a reference drug, mibefradil was used.

For accurate calcium-imagination, the light source of 4 xenon lamps in FDSS6000 were radiated to make the cells exposed selectively to the excitation wavelength (340 nm and 380 nm) by computer-controlled filter wheel. Data was obtained at interval of each 1.23 second. The emitter fluorescence light inflowed through long-pass filter was obtained as an average 340/380 ratio value for each well in the 96-wells by using CCD camera and digital fluorescence analyzer in FDSS6000. All image data and analyses were obtained by using FDSS6000-exclusive program provide from Hamamatsu Photonics.

Experimental Example 2

Measurement of IC50 for T-Type Calcium Channel Activity in HEK293 Cells Using a Electrophysiological Method 10% Fetal bovine serum (FBS) and 1% penicillin/streptomycin (v/v) were added to Dulbecco's modified Eagle's medium (DMEM), to be used as a media solution. The cells were cultured in incubator under the wet condition of 95% air/5% $CO_2$ and temperature of 36.5° C. The media solution was refreshed every 3 or 4 days, and the cells were sub-cultured every week. Only the cells which express $α_{1G}$ T-type calcium channel were cultured using G-418 (0.5 mg/ml) solution. The recording to the cells used in the T-type calcium channel activity analysis was conducted at 2-7 days after the cells were culturing on a cover slip coated with poly-L-lysine (0.5 mg/ml) when conducting every sub-culture. For analysis at a single cell level, the T-type calcium channel current was measured by an electrophysiological whole cell patch clamp method using EPC-9 amplifier (HEKA, German).

As solutions for analyzing T-type calcium channel activity, the solution comprising 140 mM of NaCl, 2 mM of $CaCl_2$, and 10 mM of HEPES (pH 7.4) was used as an extracellular solution, and the solution comprising 130 mM of KCl, 10 mM of HEPES, 11 mM of EGTA, and 5 mM of MgATP (pH 7.4)

was used as an intracellular solution. The protocol for T-type calcium channel activity which is activated at low voltage is as follows: A micro glass electrode with the resistance of 3-4 MΩ wherein the above prepared intracellular solution is filled was pricked into a single cell, to make a whole-cell recording mode. Thereafter, the cell membrane potential was fixed to −100 mV, and then the inward current due to the T-type calcium channel activity when hypopolarizing to −30 mV (50 ms duration) was measured every 10 seconds. Each compound to be tested was dissolved in 100% dimethylsulfoxide (DMSO) to make a 10 mM stock solution. The effect of the compound on T-type calcium channel current compound was initially examined in the stock solution with the 1000-times diluted concentration of 10 μM (containing 0.1% DMSO) and then examined in the solution with the concentration for $IC_{50}$ measurement (mostly 0.1 to 100 μM), to obtain $IC_{50}$ value. More specifically, the cells were treated each compound together with the extracellular solution for 30 to 60 seconds, and the inhibition level of peak current induced by the compound was calculated as percentage, to obtain the % inhibition value.

TABLE 3

| | CODE | % Inhibition [α1G, 10 μM] using FDSS6000 |
|---|---|---|
| 1 | KHG23168 | 21.63 |
| 2 | KHG23169 | 23.19 |
| 3 | KHG23170 | 30.68 |
| 4 | KHG23171 | 21.52 |
| 5 | KHG23172 | 27.58 |
| 6 | KHG23173 | 28.06 |
| 7 | KHG23174 | 18.82 |
| 8 | KHG23175 | 23.80 |
| 9 | KHG23176 | 20.52 |
| 10 | KHG23177 | 23.31 |
| 11 | KHG23178 | 34.47 |
| 12 | KHG23179 | 30.76 |
| 13 | KHG23184 | 24.87 |
| 14 | KHG23186 | 29.78 |
| 15 | KHG23187 | 21.39 |
| 16 | KHG23188 | 19.34 |
| 17 | KHG23189 | 19.29 |
| 18 | KHG23190 | 20.96 |
| 19 | KHG23191 | 18.00 |
| 20 | KHG23192 | 16.84 |
| 21 | KHG23737 | 16.07 |
| 23 | KHG23393 | 3.8 |
| 24 | KHG23380 | 11.4 |
| 25 | KHG23185 | 12.3 |
| 26 | KHG23383 | 5.7 |
| 27 | KHG23389 | 25.40 |
| 28 | KHG23396 | 3.0 |
| 29 | KHG23391 | 0.8 |
| 30 | KHG23386 | 4.5 |

TABLE 3-continued

| | CODE | % Inhibition [α1G, 10 μM] using FDSS6000 |
|---|---|---|
| 31 | KHG23390 | 11.6 |
| 32 | KHG23394 | 41.5 |
| 33 | KHG23392 | 22.7 |
| 34 | KHG23381 | 6.2 |
| 35 | KHG23384 | 6.1 |
| 36 | KHG23399 | 3.4 |
| 37 | KHG23395 | 2.7 |
| 38 | KHG23379 | 14.7 |
| 39 | KHG23385 | 5.9 |
| 40 | KHG23397 | 14.2 |
| 41 | KHG23398 | 0.2 |
| 42 | KHG23387 | 3.2 |
| 43 | KHG23382 | 24.0 |

[표 4]

| | KODE | % Inhibition [α1G, 10 μM] using FDSS6000 |
|---|---|---|
| 1 | KHG24373 | 21.67 |
| 2 | KHG24374 | 20.73 |
| 3 | KHG24375 | 19.90 |
| 4 | KHG24376 | 16.08 |
| 5 | KHG24377 | 20.17 |
| 6 | KHG24378 | 9.48 |
| 7 | KHG24379 | 16.77 |
| 8 | KHG24380 | 19.56 |
| 9 | KHG24381 | 20.77 |
| 10 | KHG24382 | 22.28 |
| 11 | KHG24383 | 21.55 |
| 12 | KHG24384 | 20.26 |
| 13 | KHG24385 | 15.78 |
| 14 | KHG24386 | 10.95 |
| 15 | KHG24387 | 17.05 |
| 16 | KHG24388 | 10.79 |
| 17 | KHG24389 | 21.86 |
| 18 | KHG24390 | 7.32 |
| 19 | KHG24391 | 20.81 |
| 20 | KHG24392 | 12.88 |
| 21 | KHG24393 | 13.43 |
| 22 | KHG24394 | 12.67 |
| 23 | KHG24024 | 13.04 |
| 24 | KHG24025 | 19.92 |
| 25 | KHG24026 | 19.77 |
| 26 | KHG24037 | 21.18 |
| 27 | KHG24038 | 14.18 |
| 28 | KHG24039 | 21.89 |
| 28 | KHG24040 | 16.22 |
| 30 | KHG24022 | 10.14 |
| 31 | KHG24041 | 13.34 |

[표 5]

| | % Inhibition on HEK293 (100 mM) | $IC_{50}$ on HEK293 |
|---|---|---|
| Mibefradil | | 0.84 |
| | 88.2 | 0.31 ± 0.22 |

| | % Inhibition on HEK293 (100 mM) | IC$_{50}$ on HEK293 |
|---|---|---|
| 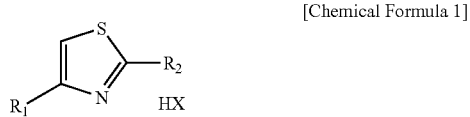 | 87.8 | 0.78 ± 0.08 |

As shown in above Tables 3, 4, and 5, it is revealed that the thiazole-based compounds of the present invention have an excellent inhibiting activity against T-type calcium channel.

Due to such excellent T-type calcium channel inhibiting activity, the thiazole-based compounds of the present invention can be used in the treatment and/or prevention of nervous diseases, pain, epilepsy, hypertension, angina pectoris, heart muscle disease, vascular disorder, and cancer, to obtain an excellent effect.

What is claimed is:

1. A thiazole-based compound represented by Chemical Formula 1:

[Chemical Formula 1]

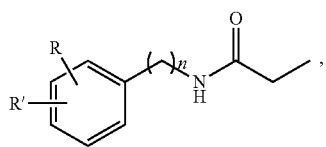

wherein,

R1 is

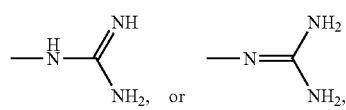,

R and R' are the same or different from each other, and independently selected from the group consisting of hydrogen atom, halogen atom, C1-C5 alkyl, alkyloxy, phenyloxy, nitro, cyano, alkoxycarbonyl, and C3-C6 cycloalkyl, n is 0, 1, or 2, R2 is —N(H)—C(=NH)—NH$_2$, or —N=C(NH$_2$)—NH$_2$, X is halogen atom.

2. The compound according to claim 1, represented by following Chemical Formula 2:

[Chemical Formula 2]

wherein,

R and R' are the same or different from each other, and independently selected from the group consisting of hydrogen atom, halogen atom, C1-C5 alkyl, alkyloxy, phenyloxy, nitro, cyano, alkoxycarbonyl, and C3-C6 cycloalkyl, n is 0, 1, or 2, X is halogen atom.

3. The compound according to claim 1, selected from the group consisting of:

[2-(2-(diaminomethyleneamino)thiazole-4-yl)-N-(2-fluoro-5-nitrophenyl) acetamide hydrochloride];

N-(2-chloro-4-fluorophenyl)-2-(2-(diaminomethyleneamino)thiazole -4-yl) acetamide hydrochloride;

N-(3-chloro-4-methylphenyl)-2-(2-(diaminomethyleneamino)thiazole -4-yl) acetamide hydrochloride;

2-(2-(diaminomethyleneamino)thiazole-4-yl)-N-(4-fluorophenyl) acetamide hydrochloride;

N-(5-chloro-2-fluorophenyl)-2-(2-(diaminomethyleneamino)thiazole -4-yl) acetamide hydrochloride;

N-(4-chloro-2-fluorophenyl)-2-(2-(diaminomethyleneamino)thiazole -4-yl) acetamide hydrochloride;

N-(2-chloro-4-methylphenyl)-2-(2-(diaminomethyleneamino)thiazole -4-yl) acetamide hydrochloride;

2-(2-(diaminomethyleneamino)thiazole-4-yl)-N-p-tolylacetamide hydrochloride;

N-(4-cyanophenyl)-2-(2-(diaminomethyleneamino)thiazole-4-yl)acetamide hydrochloride;

2-(2-(diaminomethyleneamino)thiazole-4-yl)-N-phenylacetamide hydrochloride;

N-(4-bromophenyl)-2-(2-(diaminomethyleneamino)thiazole-4-yl)acetamide hydrochloride;

2-(2-(diaminomethyleneamino)thiazole-4-yl)-N-(3-fluoro -4-methoxyphenyl) acetamide hydrochloride;

N-(4-chlorophenyl)-2-(2-(diaminomethyleneamino)thiazole -4-yl)acetamide hydrochloride;

2-(2-(diaminomethyleneamino)thiazole-4-yl)-N-(3,5-dichlorophenyl)acetamide hydrochloride;

2-(2-(diaminomethyleneamino)thiazole-4-yl)-N-(4-ethylphenyl)acetamide hydrochloride;

2-(2-(diaminomethyleneamino)thiazole-4-yl)-N-(4-methylbenzyl)acetamide hydrochloride;
2-(2-(diaminomethyleneamino)thiazole-4-yl)-N-(4-methylphenethyl)acetamide hydrochloride;
2-(2-(diaminomethyleneamino)thiazole-4-yl)-N-(3,4-difluorolbenzyl)acetamide hydrochloride;
2-(2-(diaminomethyleneamino)thiazole-4-yl)-N-(4-fluorophenethyl)acetamide hydrochloride;
N-(2-bromo-4-methylphenyl)-2-(2-(diaminomethyleneamino)thiazole -4-yl) acetamide hydrochloride;
N-(4-ethoxyphenyl)-2-(2-(diaminomethyleneamino)thiazole-4-yl)acetamide hydrochloride;
2-(2-(diaminomethyleneamino)thiazole-4-yl)-N-(4-isopropylphenyl)acetamide hydrochloride;
2-(2-(diaminomethyleneamino)thiazole-4-yl)-N-(4-nitrophenyl)acetamide hydrochloride;
N-(4-decylphenyl)-2-(2-(diaminomethyleneamino)thiazole-4-yl)acetamide hydrochloride;
ethyl 3-(2-(2-(diaminomethyleneamino)thiazole-4-yl)acetamido)benzoate hydrochloride;
2-(2-(diaminomethyleneamino)thiazole-4-yl)-N-(4-hexylphenyl)acetamide hydrochloride;
N-(4-butoxyphenyl)-2-(2-(diaminomethyleneamino)thiazole-4-yl)acetamide hydrochloride;
ethyl 4-(2-(2-(diaminomethyleneamino)thiazole-4-yl)acetamido)benzoate hydrochloride;
2-(2-(diaminomethyleneamino)thiazole-4-yl)-N-(4-hexylphenyl)acetamide hydrochloride;
N-(4-(cyanomethyl)phenyl)-2-(2-(diaminomethyleneamino)thiazole-4-yl) acetamide hydrochloride;
N-(4-butylphenyl)-2-(2-(diaminomethyleneamino)thiazole-4-yl)acetamide hydrochloride;
2-(2-(diaminomethyleneamino)thiazole-4-yl)-N-(4-phenoxyphenyl)acetamide hydrochloride;
2-(2-(diaminomethyleneamino)thiazole-4-yl)-N-(2,6-dichloro-4-(trifluoromethyl) phenyl)acetamide hydrochloride;
2-(2-(diaminomethyleneamino)thiazole-4-yl)-N-(2,3,4-trifluorophenyl)acetamide hydrochloride;
2-(2-(diaminomethyleneamino)thiazole-4-yl)-N-(4-methoxy-2-methylphenyl)acetamide hydrochloride;
N-(3,5-bis(trifluoromethyl)phenyl)-2-(2-(diaminomethyleneamino)thiazole -4-yl) acetamide hydrochloride;
2-(2-(diaminomethyleneamino)thiazole-4-yl)-N-(2,3,5,6-tetrachlorophenyl) acetamide hydrochloride;
N-(3-chloro-4-methylphenyl)-2-(2-(diaminomethyleneamino)thiazole -4-yl) acetamide hydrochloride;
2-(2-(diaminomethyleneamino)thiazole-4-yl)-N-(2,6-dichloro -4-(trifluoromethoxy) phenyl)acetamide hydrochloride; and
2-(2-(diaminomethyleneamino)thiazole-4-yl)-N-(3-fluoro-4-methoxyphenyl) acetamide hydrochloride

4. A composition for inhibiting T-type calcium channel containing the thiazole-based compound according to any one of claims 1 to 3 or pharmaceutically acceptable salt thereof as an active ingredient.

5. A food or food additive containing the thiazole-based compound according to any one of claims 1 to 3 or pharmaceutically acceptable salt thereof.

* * * * *